US005795547A

United States Patent [19]
Moser et al.

[11] Patent Number: 5,795,547
[45] Date of Patent: *Aug. 18, 1998

[54] THERMAL CYCLER

[75] Inventors: Rolf Moser, Vitznau; Lukas Birrer, Lucerne, both of Switzerland

[73] Assignee: Roche Diagnostic Systems, Inc., Branchburg, N.J.

[*] Notice: The term of this patent shall not extend beyond the expiration date of Pat. No. 5,616,301.

[21] Appl. No.: 735,943

[22] Filed: Oct. 23, 1996

Related U.S. Application Data

[63] Continuation of Ser. No. 301,932, Sep. 7, 1994, Pat. No. 5,616,301.

[30] Foreign Application Priority Data

Sep. 10, 1993 [CH] Switzerland .............. 2717/93

[51] Int. Cl.$^6$ .............. B01L 9/00; B01L 11/02
[52] U.S. Cl. .............. 422/104; 422/64; 422/67; 422/99; 435/286.1; 435/303.1
[58] Field of Search .............. 422/64, 67, 104, 422/105, 109, 99; 435/286.1, 303.1

[56] References Cited

U.S. PATENT DOCUMENTS

| 4,338,279 | 7/1982 | Orimo et al. .............. 422/67 |
| 4,865,986 | 9/1989 | Coy et al. |
| 4,933,146 | 6/1990 | Meyer et al. |
| 5,123,477 | 6/1992 | Tyler .............. 435/286.1 |
| 5,156,809 | 10/1992 | Hupe et al. .............. 422/64 |
| 5,171,531 | 12/1992 | Christianson et al. .............. 422/64 |
| 5,176,203 | 1/1993 | Larzul .............. 435/286.1 |
| 5,187,084 | 2/1993 | Hallsby .............. 435/303.1 |
| 5,207,987 | 5/1993 | Kureshy et al. .............. 422/64 |
| 5,446,263 | 8/1995 | Eigen et al. .............. 435/286.1 |
| 5,455,175 | 10/1995 | Wittwer et al. .............. 435/286.1 |
| 5,604,101 | 2/1997 | Hanley et al. .............. 435/91.2 |
| 5,616,301 | 4/1997 | Moser et al. .............. 422/104 |

FOREIGN PATENT DOCUMENTS

| 236 069 | 2/1987 | European Pat. Off. |
| 488 769 | 11/1991 | European Pat. Off. |
| 171 140 | 8/1993 | European Pat. Off. |
| 3 024 210 | 1/1982 | Germany |
| 8 804 938 | 5/1988 | Germany |
| 61-212764 | 9/1986 | Japan |
| 62-235570 | 10/1987 | Japan |
| 64-500295 | 2/1989 | Japan |
| 89/12829 | 12/1990 | WIPO |
| 91/18551 | 12/1991 | WIPO |
| 92/20778 | 11/1992 | WIPO |

OTHER PUBLICATIONS

Wyld, Radio and Electronic Engineer, "An Automatic Biochemical Analyser", vol. 42, No. 9, pp. 392–401 (Sep. 1972).

Derwent Abstract No. 86–212764, Mine Kane, "Thermostatic cell for automatic chemical analyzer, JP 61–212764 (1986).

Haff, et al., BioTechniques, vol. 10, No. 1, (1990) pp. 102–112.

*Primary Examiner*—Jan Ludlow
*Attorney, Agent, or Firm*—George W. Johnston; William H. Epstein; John P. Parise

[57] ABSTRACT

An apparatus for automatic performance of temperature cycles in a number of test tubes in which each test tube is closed by a closure and contains a predetermined volume of a liquid reaction mixture. The apparatus includes a holder, a computer-controlled automatic control system, and a device for cyclic alteration of the holder temperature. The holder has an arrangement of chambers for holding test tubes with each chamber being adapted to receive one test tube. The holder is constructed of a material of high thermal conductivity, and has an upper surface, a bottom surface and a cylindrical outer wall. Each chamber has an opening located in the upper surface of the holder. The device for cyclic alteration of the temperature of the holder is actuated by the automatic control system. By reducing the dimensions of the device and the power required to operate it, numerous advantages are realized. Such advantages are achieved through the arcuate arrangement of chambers in the holder, and the test tube closure which is piercable by a pipetting needle.

13 Claims, 12 Drawing Sheets

THERMAL CYCLER

This application is a continuation of application Ser. No. 08/301,932, filed Sep. 7, 1994, now U.S. Pat. No. 5,616,301.

BACKGROUND OF THE INVENTION

1. Field

The invention relates to a thermal cycler apparatus for automatically performing temperature cycles in a number of test tubes which are each closed by a closure and contain a predetermined volume of a liquid reaction mixture.

More particularly, the invention relates to a device which is suited for use as an integrated component of an automatic analytical device for performing polymerase chain reaction.

2. Description

A device of the aforementioned kind is described in EP-A-0 236 069 A2. In this known device, test tubes are disposed in a matrix which makes it difficult to obtain a uniform temperature among all the test tubes. The device constructed as per EP-A-0 236 069 A2 is relatively bulky and requires relatively high power for operation, making it unsuitable for use as an integrated component of a modern automatic analytical device.

Devices of the initially-mentioned kind are called "thermal cyclers," and this term is used herein.

An aim of the present invention, therefore, is to provide a thermal cycler having minimum dimensions and requiring minimum power to operate.

According to the invention, this problem is solved by having the chambers in the holder disposed in a ring-like configuration, with the closure of each test tube being piercable by a pipetting needle.

Main advantages of the inventive device are that it has relatively small dimensions, requires relatively little power in operation, and is suitable for use as an integrated component of an automatic analytical device.

SUMMARY OF THE INVENTION

A device for automatic performance of temperature cycles on a number of test tubes that are closed by a piercable closure and contain a predetermined volume of a liquid reaction mixture is provided. This device comprises a holder, a computer-regulated automatic control system, and means for cyclic alteration of the temperature of the holder. The holder is formed of a material has high thermal conductivity and has an upper surface, a lower surface and a cylindrical outer wall. The holder has a ring-like arrangement of chambers for holding test tubes equiped with piercable closures, and is configured and dimensioned so that the piercable closures can be accessed by a pipetting needle. Each chamber has an opening located in the upper surface of the holder, and is configured and dimensioned to receive the lower part of a test tube. The means for cyclic alteration of the temperature of the holder is actuated by the computer-regulated automatic control system.

The means for cyclic alteration of the temperature of the holder typically includes a cold- and heat-producing element in the form of at least one Peltier element which is in thermal contact with the bottom surface of the holder.

The Peltier element is generally pressed against the holder by a central spring-biased securing means, the securing means comprising a spring pressed by a screw, which serves to adjust the tension on the spring. Oftentimes it is beneficial when the means for cyclic alteration of the temperature of the holder includes at least one Peltier element which is used exclusively as a cold-producing (heat dissipating) element and which is in thermal contact with the bottom surface of the holder.

Another preferred embodiment includes a hinged lid having a heating element for heating the closed test tubes held in the holder. The lid is provided with an opening for each chamber so that a pipetting needle can traverse the opening to pierce the closure on the test tube in the chamber. The hinged lid may further contain a closing and pressure means for securing the test tubes disposed in the holder.

The device may also include a heating element disposed around the holder along the periphery of the cylindrical outer wall of the holder, and means for recognizing a marking on an arrangement of test tubes.

A lifting-out device can facilitate removal of test tubes from the chambers in the holder. The lifting-out device comprises an ejection lever having one end connected to a hinge of the lid and the other end free. An ejection disc may also be secured to the lever. This ejection disc is typically concentric with the axis of symmetry of the holder, and has a peripheral arrangement of recesses for removing the test tubes from the chambers.

BRIEF DESCRIPTION OF THE FIGURES

An embodiment of the invention will now be described with reference to the accompanying drawings, in which.

DETAILED DESCRIPTION OF THE INVENTION

The subject invention will now be described in terms of its preferred embodiments. These embodiments are set forth to aid in the understanding of the invention, but are not to be construed as limiting.

Thermal cycler

In the following description, "thermal cycler" denotes a device for automatic performance of temperature cycles in at least one test tube 21 closed by a closure and holding a predetermined volume of a liquid reaction mixture.

The following is a description of a thermal cycler according to the invention, suitable preferably as a component of an automatic analytical device for performance of the polymerase chain reaction. The analytical device is designed, for example, for immunoassays.

Figure 1:
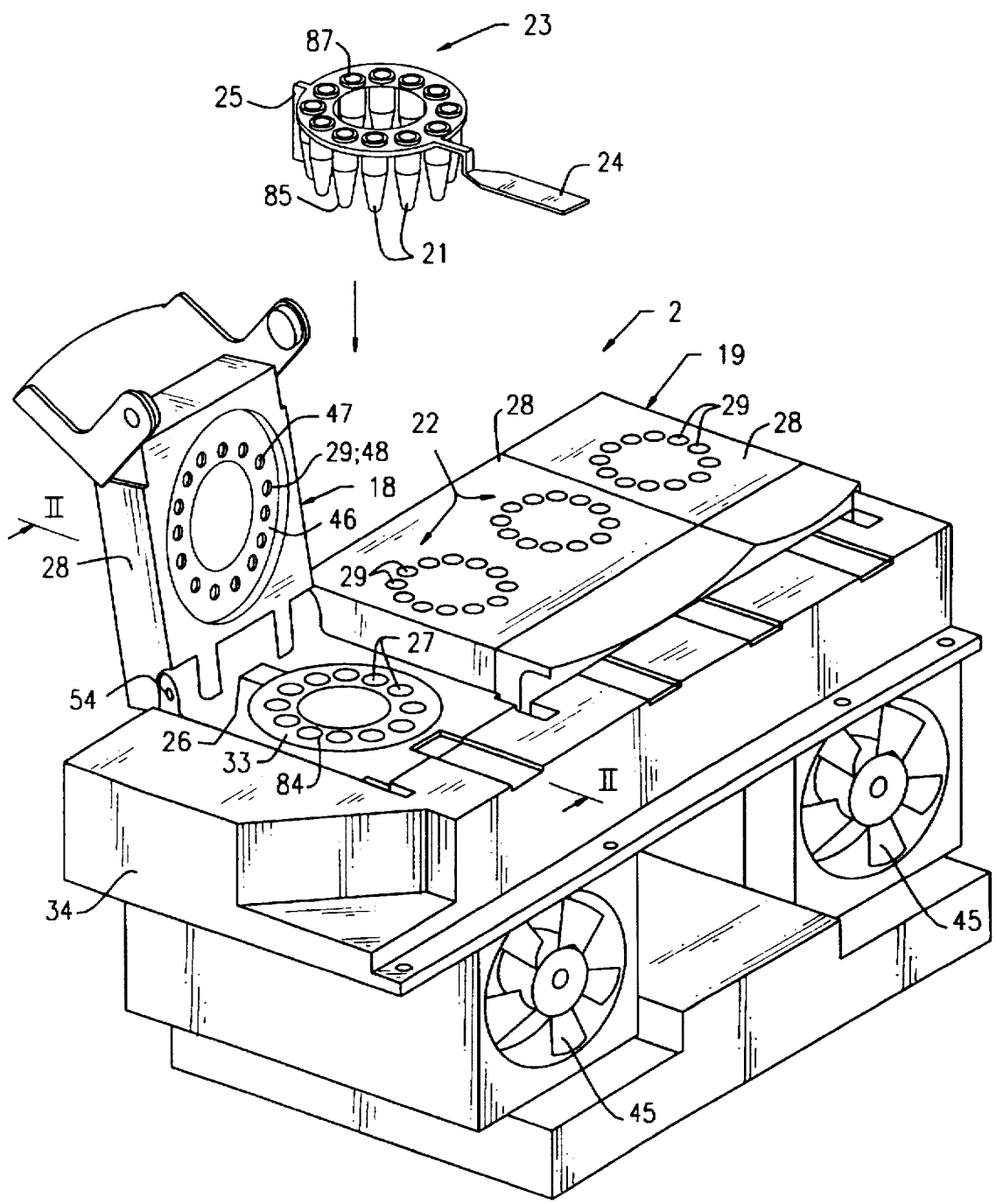
FIG. 1 shows a thermal cycler part 2 taken out of an analytical device and containing thermal cyclers 18, 19 according to the invention, the thermal cycler 18 being opened and a ring 23 of test tubes taken therefrom being shown.
Figure 13:
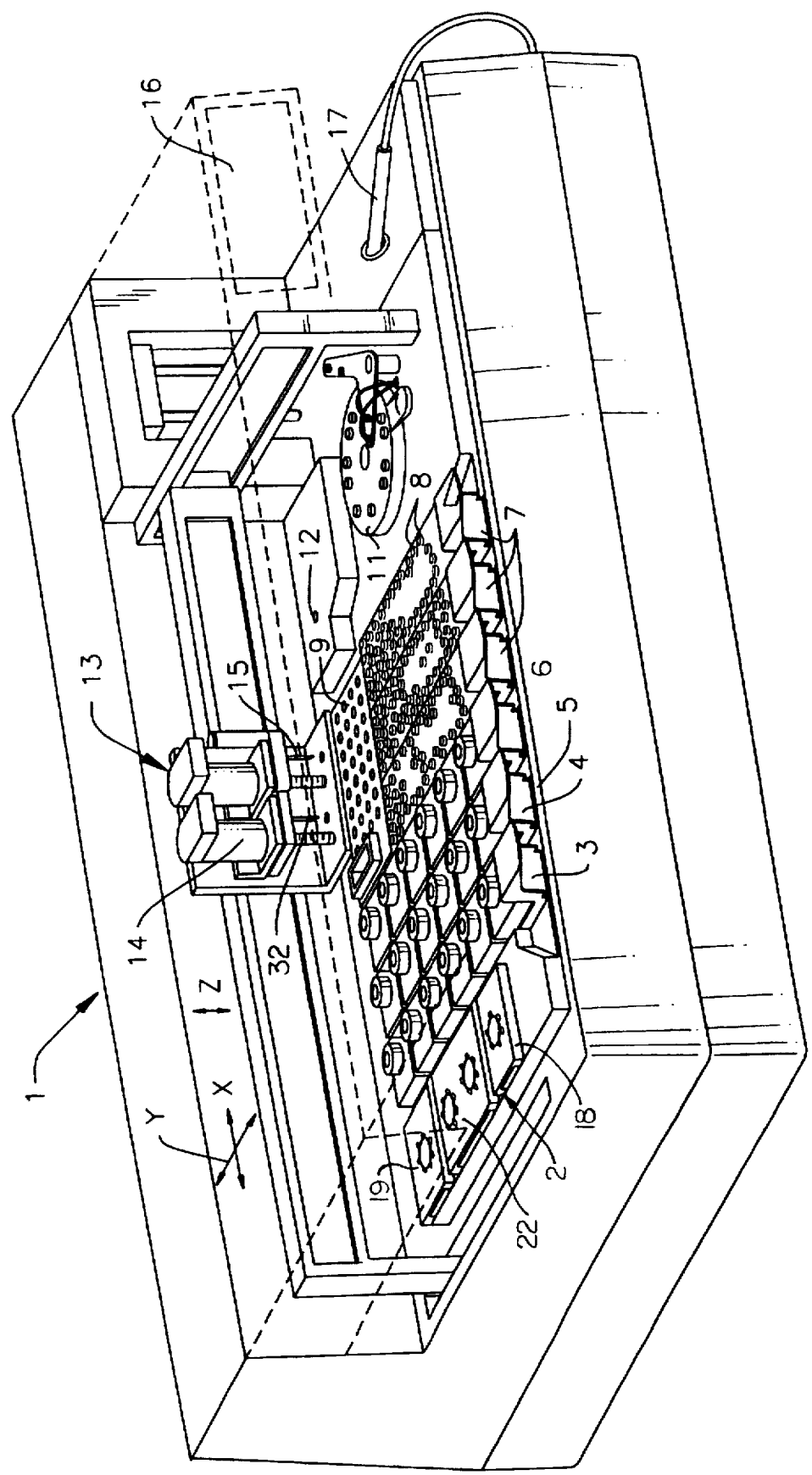
FIG. 13 is a perspective overall view of an analytical device, one component of which is a thermal cycler part 2 according to the invention.

FIG. 1 shows a thermal cycler part 2 when dismantled from an analytical device 1 as per FIG. 13. The thermal cycler part 2 contains for example, two identical thermal cyclers 18, 19 and a standby station 22. The following description of the thermal cycler 18 also applies to the thermal cycler 19.

Figure 6:
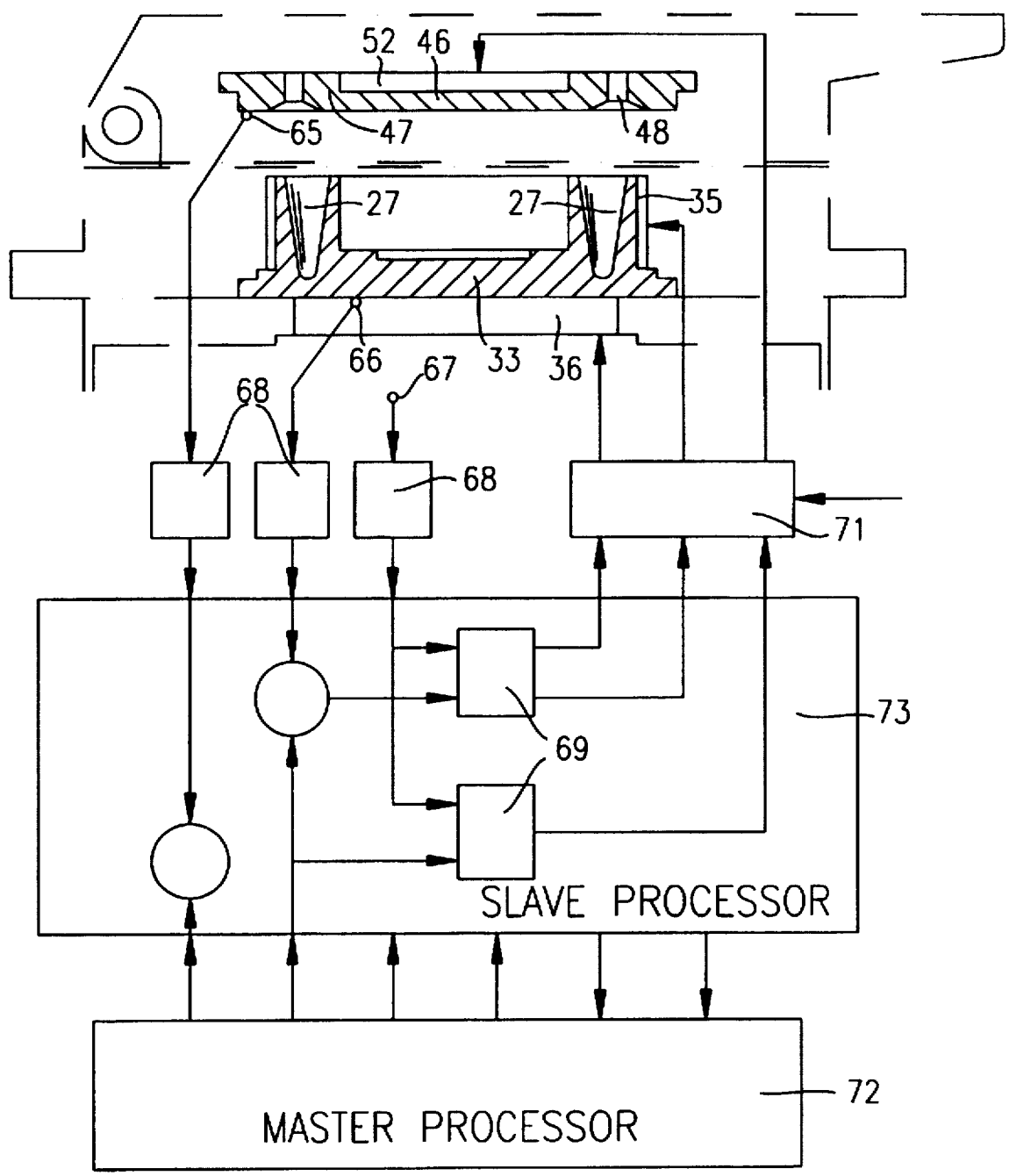
FIG. 6 is a diagram of a "master-slave" control system for regulating and monitoring the operating parameters of a thermal cycler according to the invention.
Figure 7:
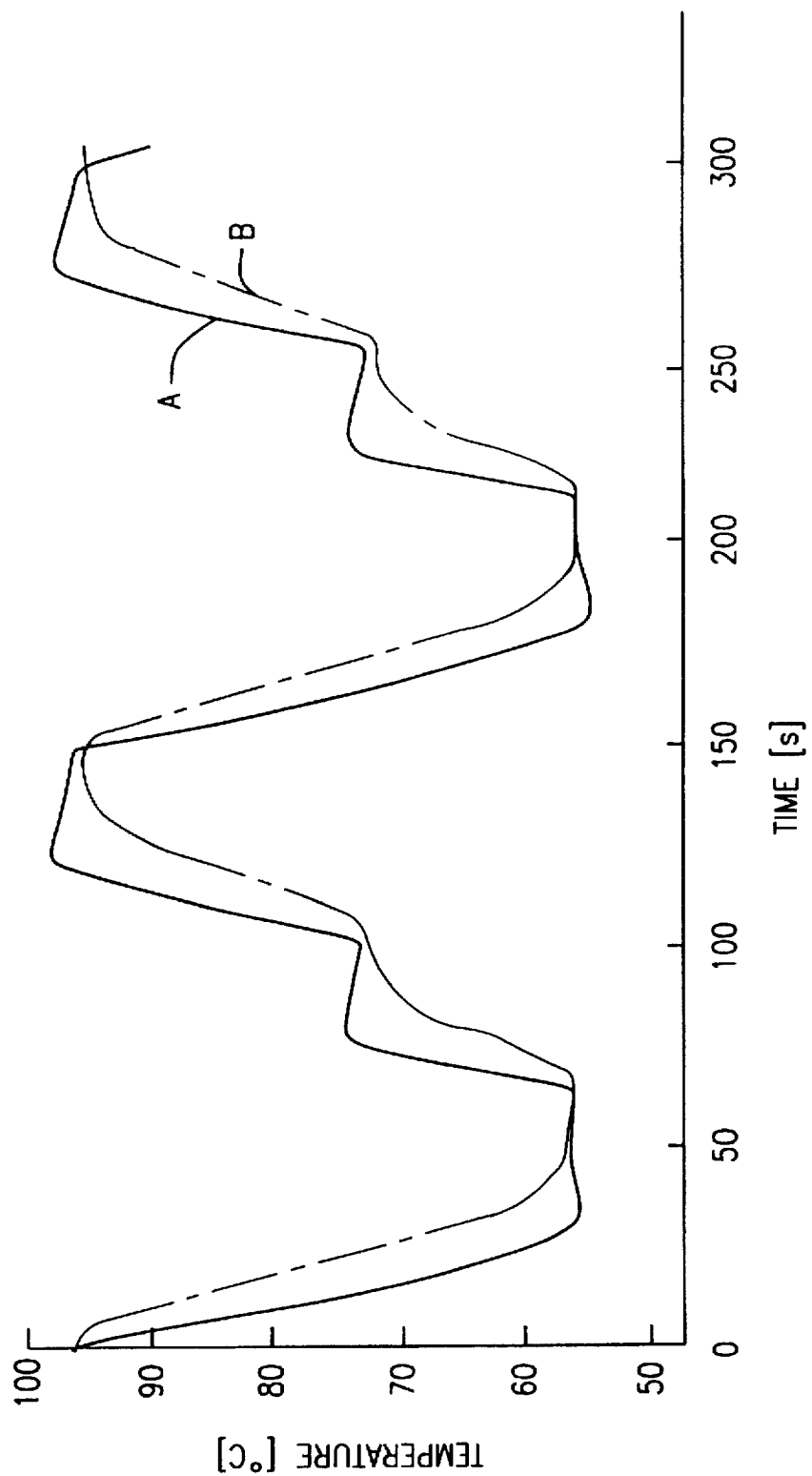
FIG. 7 is a temperature-time graph of a temperature curve stored in the master processor, or of the resulting temperatures of the unit heater and the sample.

The thermal cycler 18 contains the following components:

a) a unit heater 33 which holds the test tubes and has an annular arrangement of recesses 27, each recess serving as a chamber for holding the lower part of a test tube 21;

b) a computer-controlled automatic control system shown in FIG. 6; and c) heating or cooling elements controlled by the automatic control system and used for cyclic alteration of the temperature of the unit heater 33.

The unit heater 33 is constructed of a material having high thermal conductivity, preferably employing an aluminum or silver body.

The unit heater 33 has an upper surface, a bottom surface and a cylindrical outer wall, and each of the recesses 27 of the unit heater has an opening located in the upper surface of the unit heater.

Figure 3:
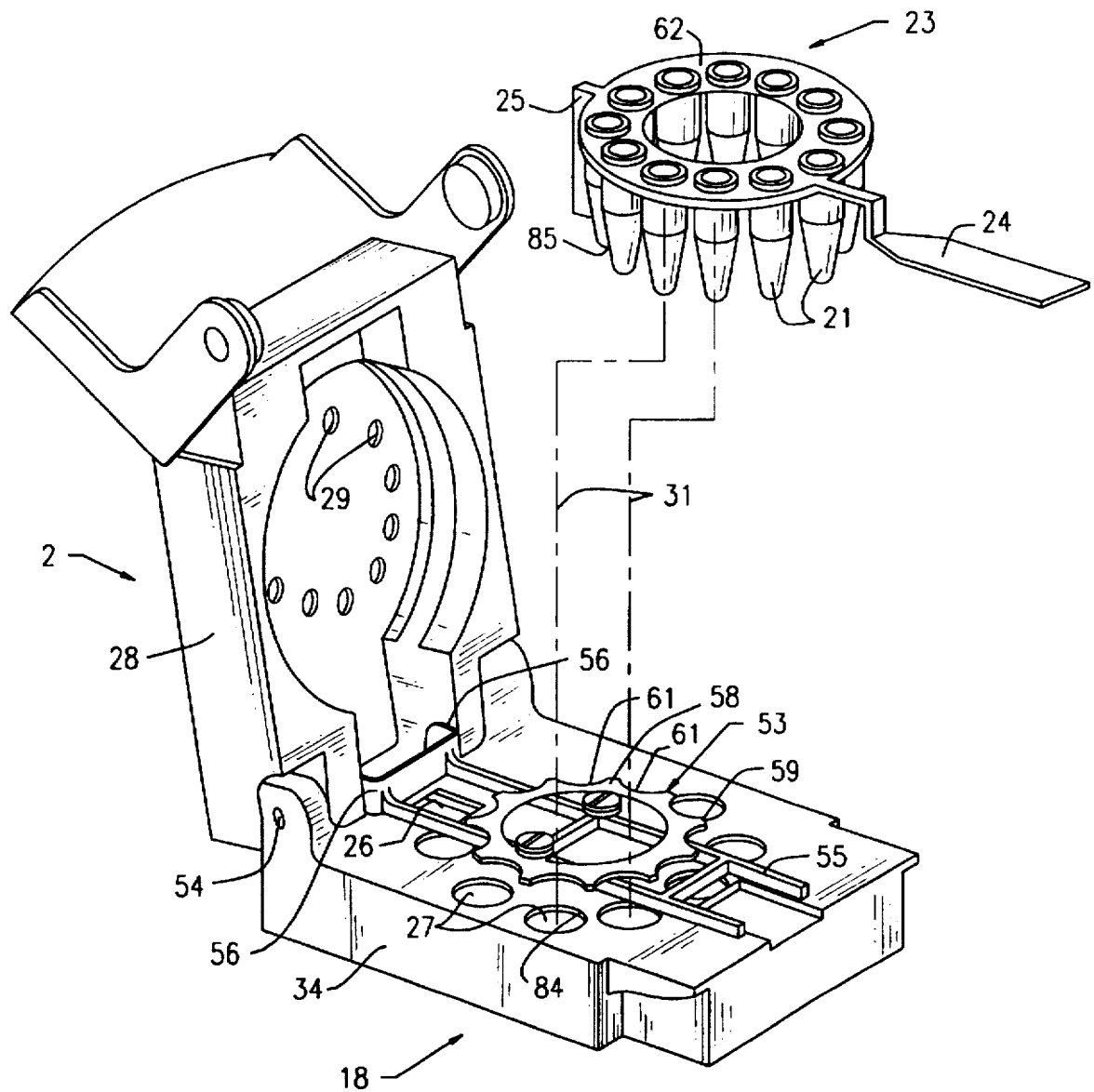
FIG. 3 is a perspective view of the thermal cycler 18 in FIG. 1, including a lifting-out device 53.

As shown in FIGS. 1 and 3, twelve test tubes 21, for example, are combined in a ring 23 of test tubes.

The test tubes 21 are conical in their lower region and cylindrical in their upper region and closed in sealing-tight manner by a lid 87. Thus, insertion of the lid 87 into a test tube 21 should form a gas-tight seal. As clearly shown in FIGS. 1 and 3, a test tube arrangement 23 of this kind can be inserted into corresponding recesses 27 in the unit heater 33 of the thermal cycler 18.

Access to the contents of a test tube

Figure 2:
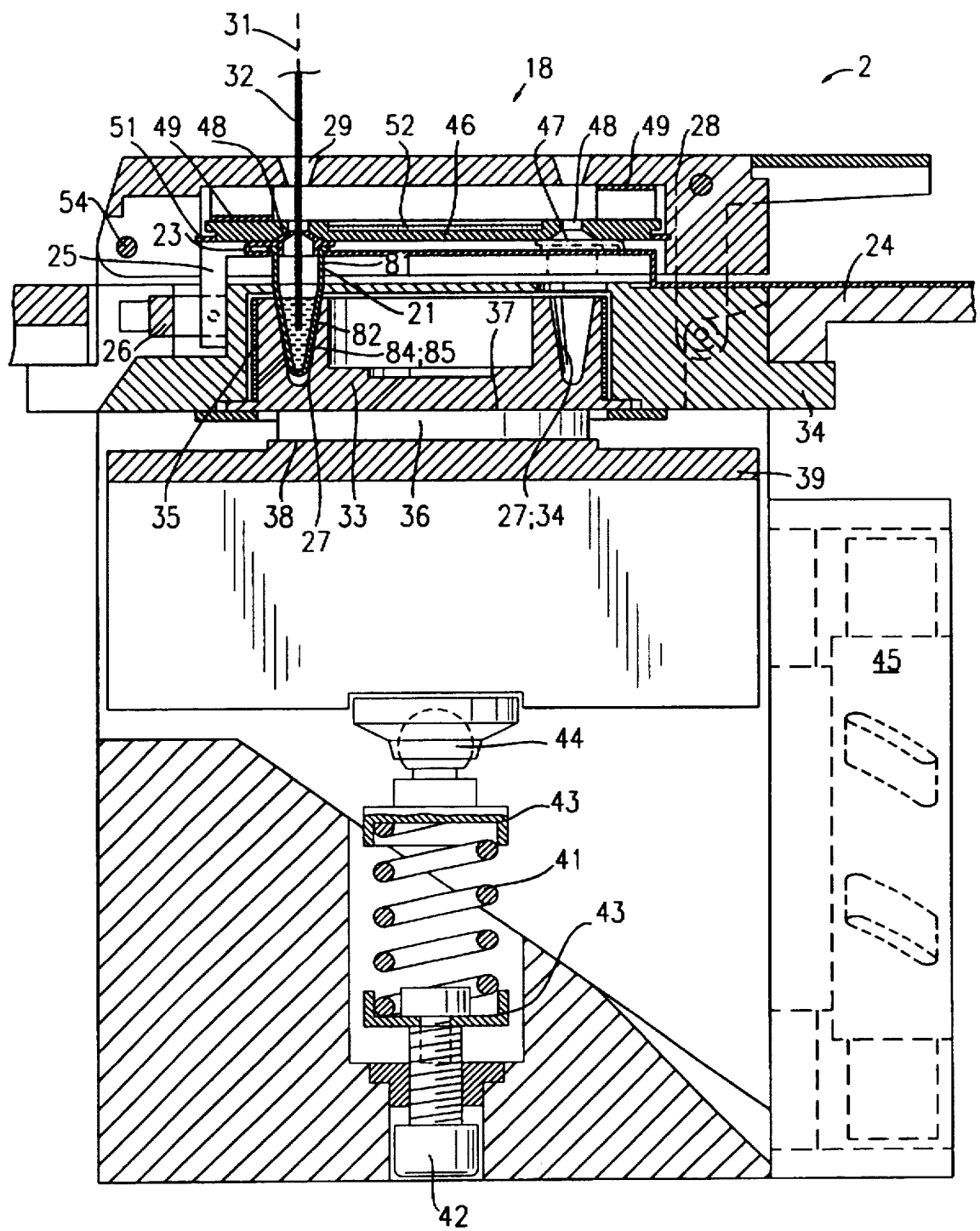
FIG. 2 is a section through line II—II in FIG. 1, the thermocycler 18 being closed.

The thermal cycler 18 has a hinged lid 28 formed with an opening 29 for each recess 27 in the unit heater 33, enabling a pipetting needle to pierce the closure 87 of the test tube 21 inserted into the recess. As shown in FIG. 2, when the hinged lid 28 is in the closed position, each opening 29 is in line with the longitudinal axis 31 of the corresponding test tube 21.

The openings 29 in the hinged lid 28 give access to the contents of each test tube when the hinged lid 28 is closed. To this end the pipetting needle 32 of a pipetting device (not shown in FIG. 3) is inserted through one of the openings 29, the lid 87 of the test tube 21 is pierced by the needle 32, and a defined volume of liquid in the test tube is then withdrawn by suction.

Heat transfer between the unit heater and the test tube

As shown in FIG. 2, the recesses 27 in the unit heater 33 are adapted to the conical region of the test tubes 21, so that the peripheral wall of the test tubes 21 reliably abuts the inner wall of the recess 27, for optimum heat transfer. In order to increase the thermal reaction speed, precision and homogeneity, the unit heater 33 is substantially heat insulated, secured in a casing 34, and has a small mass and good heat conductivity.

Heating element in the hinged lid of the thermal cycler

The lid 28 preferably contains a heating element, for example, an electric resistance heater 52 for heating the sealed test tubes disposed in the unit heater 33.

In a first embodiment of the thermal cycler, the electric resistance heater 52 is used in combination with a Peltier element 36 described hereinafter, in order to obtain a desired temperature profile (a temperature curve during a defined time interval) in the unit heater 33. In this embodiment the Peltier element, depending on the temperature to be obtained, is used as a cooling or a heating element within a temperature profile.

The electric resistance heater 52 and the Peltier element 56 are used in combination to obtain the required speed of the temperature changes in the unit heater 33 and the required precision and homogeneity of the temperature distribution. Another effect of the resistance heater 52 is to prevent any condensate forming in the lid region of the test tube 21.

Device for closing and pressing the hinged lid of the thermal cycler

The hinged lid 28 preferably contains a closing and pressing device for securing the sealed test tubes 21 disposed in the unit heater 33. To this end the hinged lid 28 has a springheld pressure plate 46, which presses each test tube 21 with a defined force into the recesses 27 in the unit heater 33. Recesses 47 for holding the cap-shaped lids 87 of the test tubes 21 and openings 48 for piercing by the pipetting needles 32 are provided in the pressure plate 46 coaxially with the test tubes 21. The spring element can be a corrugated washer 49. A safety ring 51 prevents the pressure plate 46 falling out when the hinged lid 28 is opened.

The aforementioned resistance heater 52 is preferably contained in the resilient pressure plate 46.

A cooling or heating element in the form of a Peltier element

As shown in FIG. 2, a thermal cycler 18 preferably contains at least one Peltier element 36 forming part of the means provided in the thermal cycler 18 for cyclic alteration of the temperature of the unit heater 33. One heat transfer surface 37 of the Peltier element 36 is in contact over a large area with the bottom surface of the unit heater 33 and the other heat transfer surface 38 is in contact over a large area with a cooling member 39 for heat dissipation. The cooling member 39 is preferably of aluminum or copper. A switchable fan 45 is provided for heat dissipation.

The Peltier element 36 diagrammatically shown in FIG. 2 is preferably an arrangement of such elements.

In the aforementioned first embodiment of the thermal cycler, the Peltier element 36 is used as a cooling or a heating element. This method of operating the Peltier element 36 and cooperation between it and the electric resistance heater 52 enable the required temperature of the unit heater to be reached within a temperature profile.

To prolong its life, the Peltier element 36 is preferably protected from thermodynamic mechanical tension peaks by a central spring-biased securing means which presses the Peltier element and holds it against the unit heater 33. To this end the Peltier element is resiliently clamped between the heat transfer surfaces of the unit heater 33 and the cooling member 39. The contact surface of the cooling member 39 is pressed, for example, by a pressure spring 41, against the Peltier element 36. The spring tension can be adjusted via a screw 42, a spring washer 43 and a ball and socket joint 44, which further increases the degrees of freedom of the cooling member 39.

A cooling or heating element in the form of a Peltier element

In a modified version of the embodiment described above, Peltier element 36 is used exclusively as a cold-producing (heat removal) element. That is, it is only used for cooling the heater unit 33. In this way a prolongation of the useful life of the Peltier element is obtained.

An additional heating element around the unit heater

In a second embodiment, the thermal cycler preferably incorporates an electric resistance heater 35 disposed around the heater unit 33 and along the periphery of the cylindrical outer wall of the unit heater 33. When the additional heating element is used in the thermal cycler, the Peltier element 36 is used only for cooling. This has the advantage of relieving the Peltier element from mechanical thermal stress and thus contributes to prolonging the service life of the Peltier element in the thermal cycler.

Means for recognizing a marking on the ring of test tubes

The thermal cycler 18 also contains means for recognizing a marking on the arrangement of test tubes 23, for example, marking in the form of a vertical lug 25. The lug cooperates with a detection device 26 inside the thermal cycler 18, to facilitate recognition of the presence of the ring of test tubes 23 in the thermal cycler 18. The detection device 26 is, for example, a light barrier. Also, the lug 25 permits the test tube arrangement 23 to be positioned only once in the unit heater 33. This single positioning can be combined with numbering on the seals of the test tubes, to obtain a one-to one correlation between samples and patients.

The test tube arrangement 23 also comprises a flap 24 serving for example, as a surface for carrying data on the contents of the samples in the arrangement 23, the data being present for example, in the form of a bar code.

Lifting-out device

As a result of the temperature changes and the action of spring 49, the conical regions of the reaction containers 21 may adhere to the walls of the recesses 27 in the unit heater 33. The resulting non-positive connection makes it difficult to remove the reaction containers 21 from the thermal cycler 2. For this reason, in the embodiment depicted in FIGS. 3 to 5, a lifting-out device 53 is provided to facilitate removal of the reaction-container ring 23 out of the thermal block 33.

Figure 4:
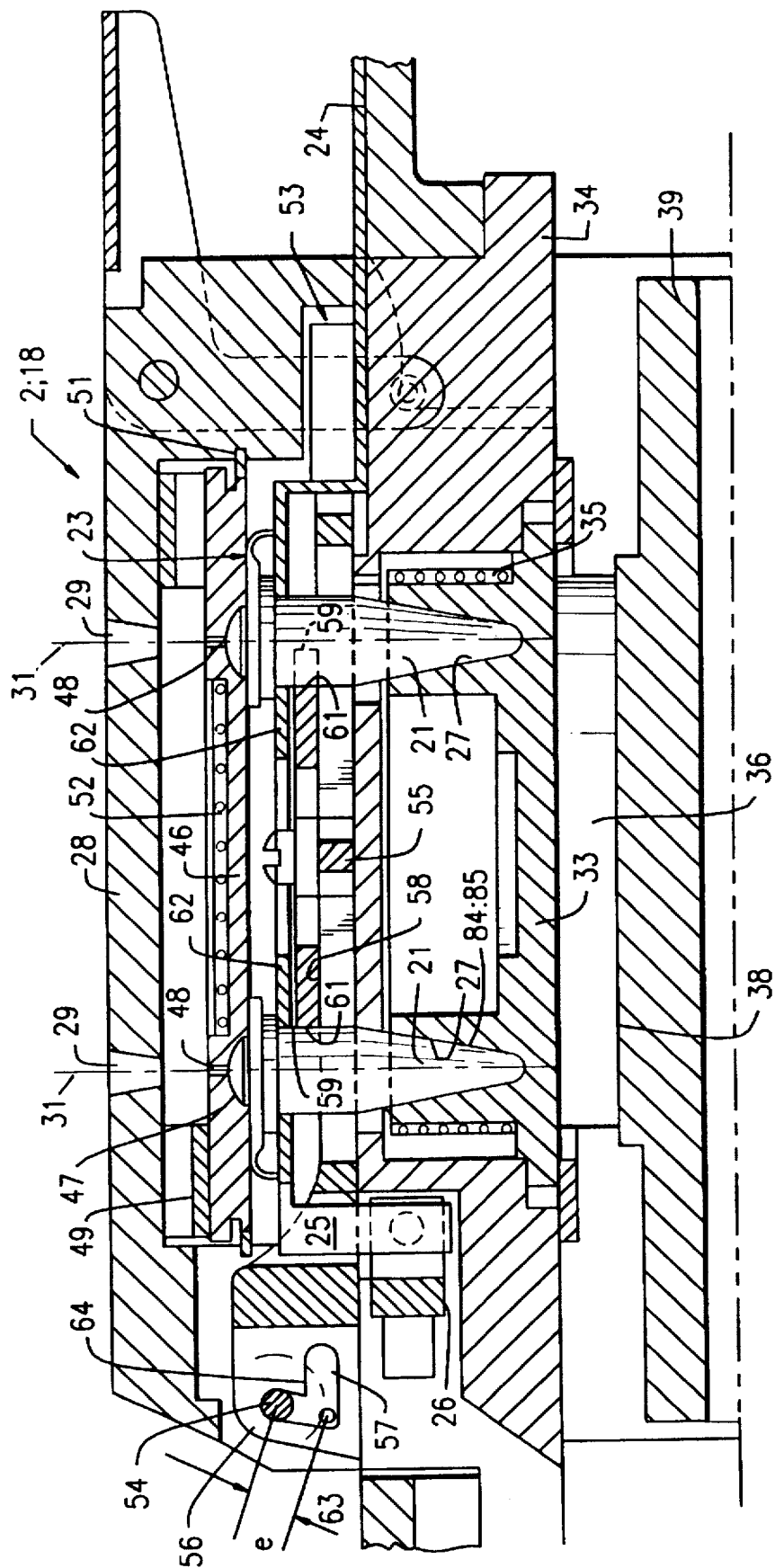
FIG. 4 is a section on a larger scale than in FIG. 2, through the thermal cycler in the closed state.
Figure 5:
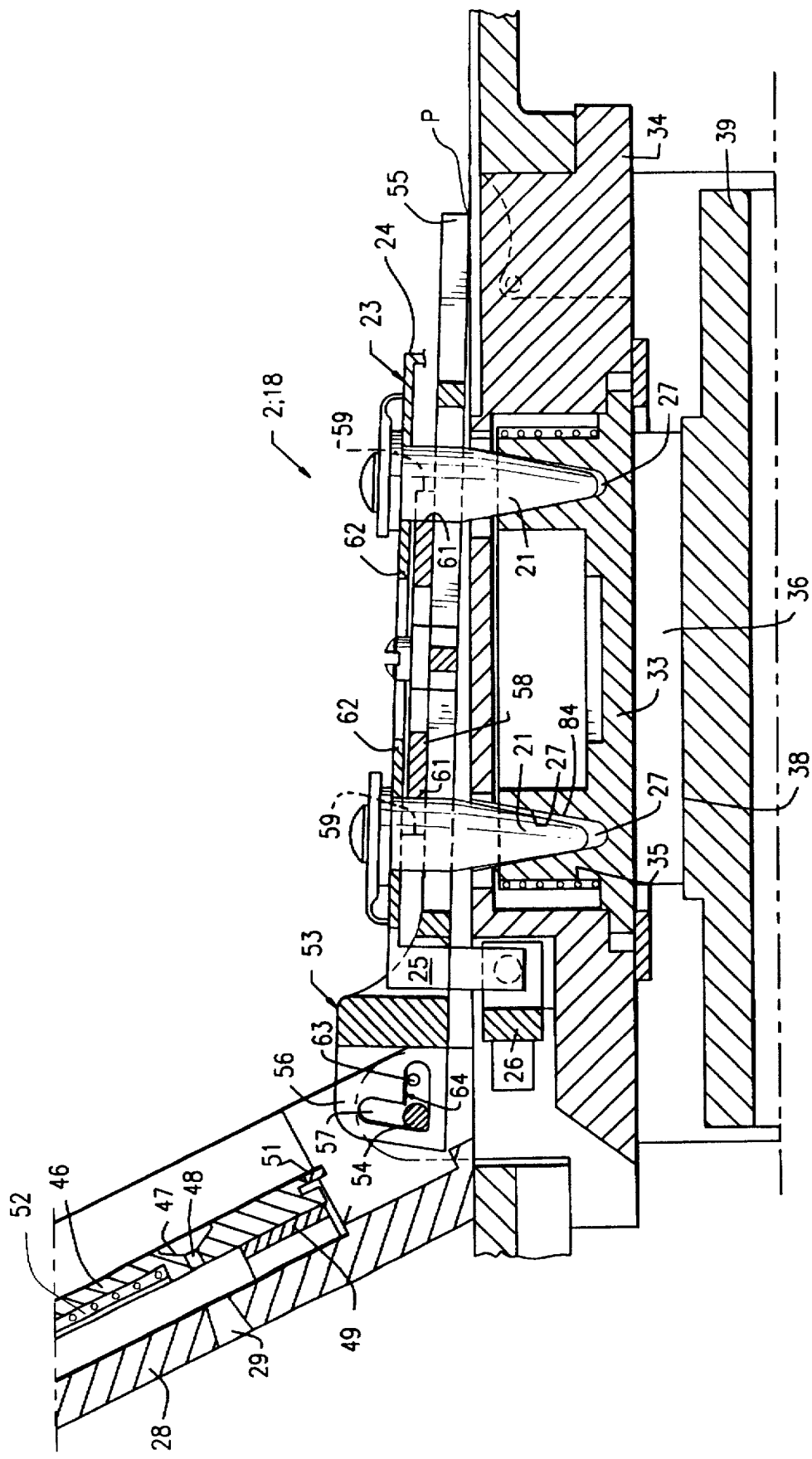
FIG. 5 shows a thermal cycler according to FIG. 4 in the open state.

As shown in FIGS. 3 to 5, the lifting-out device 53 contains a rocker 55 which serves as an ejection lever. One end of the rocker 55 is connected to a hinge of the lid 28. The other end of the rocker 55 is free. The lifting-out device 53 also contains an ejection disc 58 which is concentric with the axis of symmetry of the unit heater 33 on which the rocker 55 is disposed. On its periphery, the ejection disc 58 has an arrangement of recesses 61 for removing the reaction container ring 23 from the recesses 27 in the unit heater 33.

As shown in FIG. 3, the rocker 55 is guided on the pivot 54 of the hinged lid 28. The pivot side the rocker 55 has two lugs 56 with recesses 57 in which the pivot 54 engages. The ejection disc is screwed to the rocker 55. On its peripheral edge 59, the disc 58 has semicircular recesses 61 which are exactly aligned with the projection of the recesses 27 in the unit heater 33 or the cylindrical regions of the reaction containers 21 inserted in the recesses 27 (FIG. 5). The peripheral edge 59 of the disc 58 thus extends under the inner flange-like region 62 of the reaction-container ring 23 or the flanges on the containers 21. FIGS. 4 and 5 show the shape and function of the recess 57 in the lugs 56 of rocker 55 in conjunction with the pivot 54 of the lid 28 and a control pin 63 disposed at a distance e on the lid 28 and likewise engaging in the recess 57. When the lid 28 is closed, the lifting-out device 53 is inoperative. When the lid 28 is opened beyond a certain angle, the pin 63 comes into contact with a control surface 64 on the recess 57 and pivots the rocker 55 around the point P, thus lifting the sample-containers 21. As a result of the tilting of the rocker 55 around the point P or the increasingly sloping position of the disc 58, the breaking loose forces associated with the individual reaction containers 21 are offset in time, so that the containers 21 are progressively loosened from their recesses 27. The force applied and the stress on the material is thus kept at a low level and operation is more comfortable.

Automatic control of the thermal cycler

FIG. 6 is a diagram of an automatic control system of a thermal cycler 18 according to the invention, via master/slave processors 72 and 73.

The temperature of the pressure plate 46 of the lid 28, and of the unit heater 33 and the environment is detected by sensors 65, 66, 67 and supplied via a temperature interface 68 to the slave processor 73. The set temperatures, set times, number of temperature cycles and speed of the heating and cooling processes inter alia are input into the master processor 72 (the interface to the user).

Predetermined stored temperature/time profiles can be selected and run. Input is via a keyboard 16 or another interface. These data are supplied to the slave processor 73, which via controllers 69 actuates a power output stage 71 which in turn controls the supply of energy to the heating elements 55, 52 and the Peltier element 36. Feedback (actual values) are supplied via the slave processor 73 to the master processor 72, where they are processed or displayed to the user. In this manner, the user is informed of the instantaneous temperature of the samples, the temperatures already reached, giving times, and the temperatures still to be reached, giving times.

The operating state of the system is permanently monitored and recorded. Faults which cannot be eliminated by the system, result in automatic switching-off or a fault alarm.

The temperature of the sample is computed from the temperature of the unit heater 33. To this end the transfer function from the sample chamber to the sample in the reaction container 21 is determined. This function is substantially a low-pass filter with idle time.

Suitable control algorithms (scanned systems) are used to calculate the respective controller output necessary for adjusting the temperature of the sample to the preset temperature. These calculations are made by a signal processor. The calculated controller output is supplied in the form of a pulse width to the power output stage 71. The power output stage 71 is for example, a power FET with a suitable protective and anti-interference circuit.

The previously-described automatic control system is for using the thermal cycler for heating and cooling samples in accordance with given temperature profiles, in a ring of reaction containers inserted into the thermal cycler. The temperature profiles are defined by plateau temperatures of defined duration, and the gradient defining the time at which a plateau temperature must be reached. This means that all samples in the thermal cycler must be at the same temperature at the same time.

Figure 8:
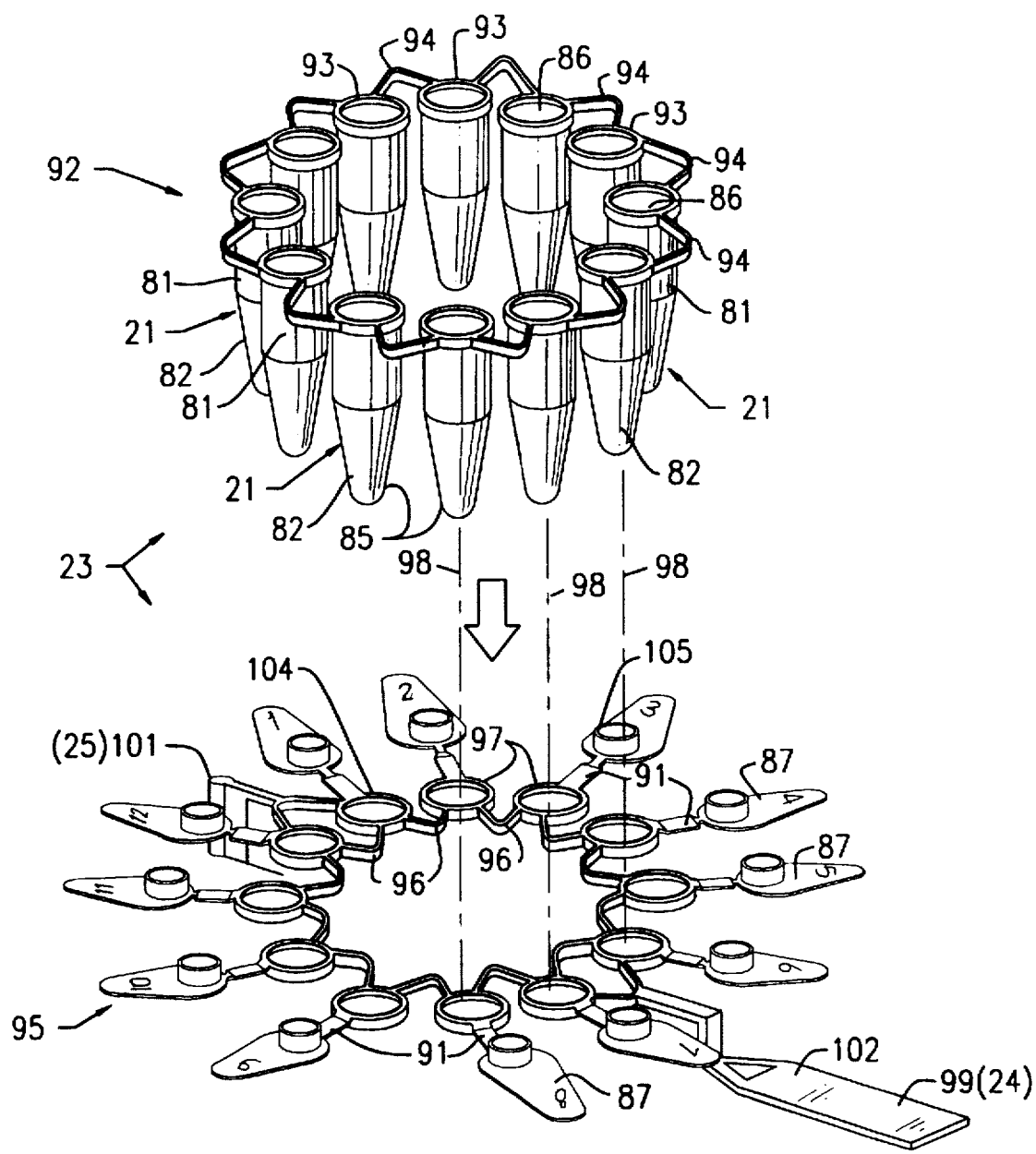
FIG. 8 is a perspective exploded view of the individual parts 19 to 95 of a test tube arrangement 23 for use in a thermal cycler according to the invention.
Figure 9:
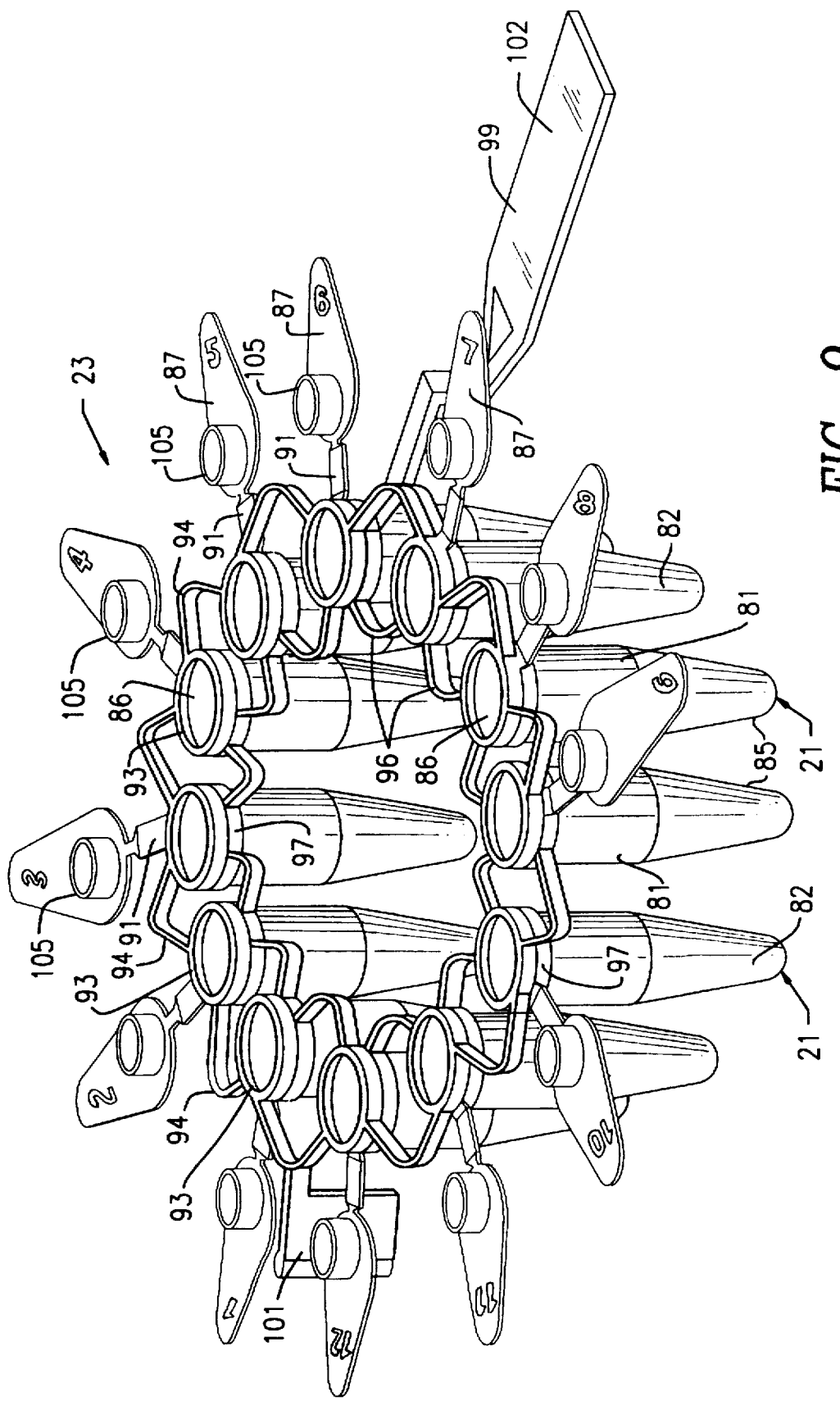
FIG. 9 shows the individual parts 92 to 95 in FIG. 8, when assembled and with the test tubes in the resulting test tube arrangement 23 in the open state.

FIG. 8, by way of example, shows temperature curves in a cyclic process. Curve A shows the temperature at the unit heater 33, and curve B shows the temperature of the liquid in the reaction container 21. The thermal cycler can be used for setting temperatures between about 40° C. and about 98° C. Typically the lower temperatures are between about 50° C. and about 60° C. and the upper temperatures between about 90° C. and about 96° C. When the average temperature is used, it is around 72° C. The rate of heating and cooling by the thermal cycler is about 1° C. per second. A typical cycle lasts about 120 seconds. When the corresponding temperatures have to be held for longer than about 10 seconds, the cycle is prolonged accordingly.

Test tubes

As shown more particularly in FIGS. 8 to 12, the test tubes 21 have a conical lower region 82 and a cylindrical upper region 81. The conical lower region 82 of the test tube 21 containing the sample for heat-treatment has a thinner wall, for better heat transfer, than the upper cylindrical region 81. As FIG. 3 shows, the lower conical region 82 of the test tube 21 can be inserted with an exact fit into the correspondingly shaped recess 27 in the unit heater 33 of the thermal cycler 18, so that the conical inner wall of the recess 27 is fully in contact with the conical outer wall 85 of the bottom region 82 of the test tube 21, thus ensuring optimum heat transfer.

The opening 86 of the test tube 21 can be closed in sealing-tight manner by a lid 87 to form, preferably, a gas-tight seal. The lid 87 can be perforated by a pipetting needle 32 for drawing some sample material.

To reduce expense and facilitate handling of the test tubes 21, a number of test tubes (for example, twelve) are combined in a unit, for example, in a circular arrangement to form a ring of test tubes, and the lid 87 is non-detachably secured by a film hinge 91. Alternatively, a semicircular or other arcuate arrangement is possible.

Advantageously, the arrangement 23 of test tubes can be made in two parts. One part 92 consists of test tubes 21 spaced at uniform angular intervals and connected in a circle by thin webs 94 on flange-like larger-diameter portions 93 at the opening end. The webs 94 are V-shaped so that the ring 92 of test tubes has radially flexibility, which is advantageous when joining to the other part 95. The part 92 is preferably made of polypropylene (PP).

The other part 95 of the test tube arrangement 23 comprises rings 97 disposed in a circle and interconnected by webs 96, the inner diameter of the rings being identical with the outer diameter of the cylindrical regions 81 of the test tubes 21, and the centers of the rings being in line with the longitudinal axes 98 of the test tubes 21. The webs 96 are V-shaped, to maintain radial elasticity. Radially outwardly extending film hinges 91 are integrally formed on the rings 97 and each end in a closure lid 87. Part 95 is preferably also made of polypropylene (PP).

Two radially outwardly extending, diametrically opposite extensions 99 and 101 are formed on the other part 95 and offset by half the spacing angle between the rings 97. One extension 99 has a horizontal surface 102 on which, for example, data on the samples in the test tubes 21 can be recorded in a bar code. The other extension 101, in the form of a vertical lug, cooperates with a detector 26, for example, a light barrier, in the thermal cycler 18 (see FIG. 1). By this means, the test tube arrangement 23 is automatically inserted in a defined position into the thermal cycler 2.

To facilitate supervision by the operator, the sample number can be disposed on the lid flaps of the test tubes.

Figure 10:
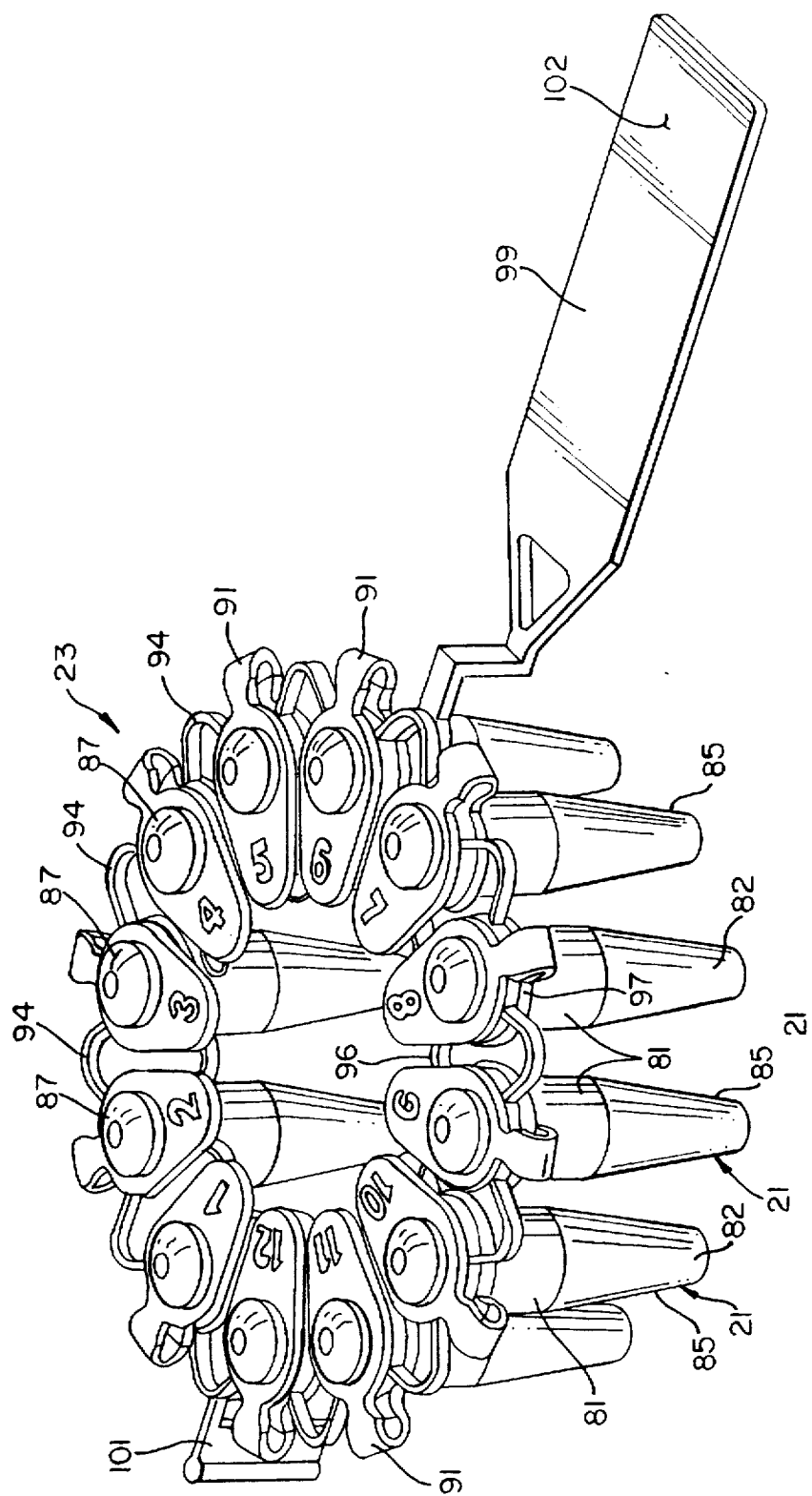
FIG. 10 shows the individual parts 92 to 95 in FIG. 8, when assembled and with the test tubes in the resulting arrangement 23 in the closed state.
Figure 11:
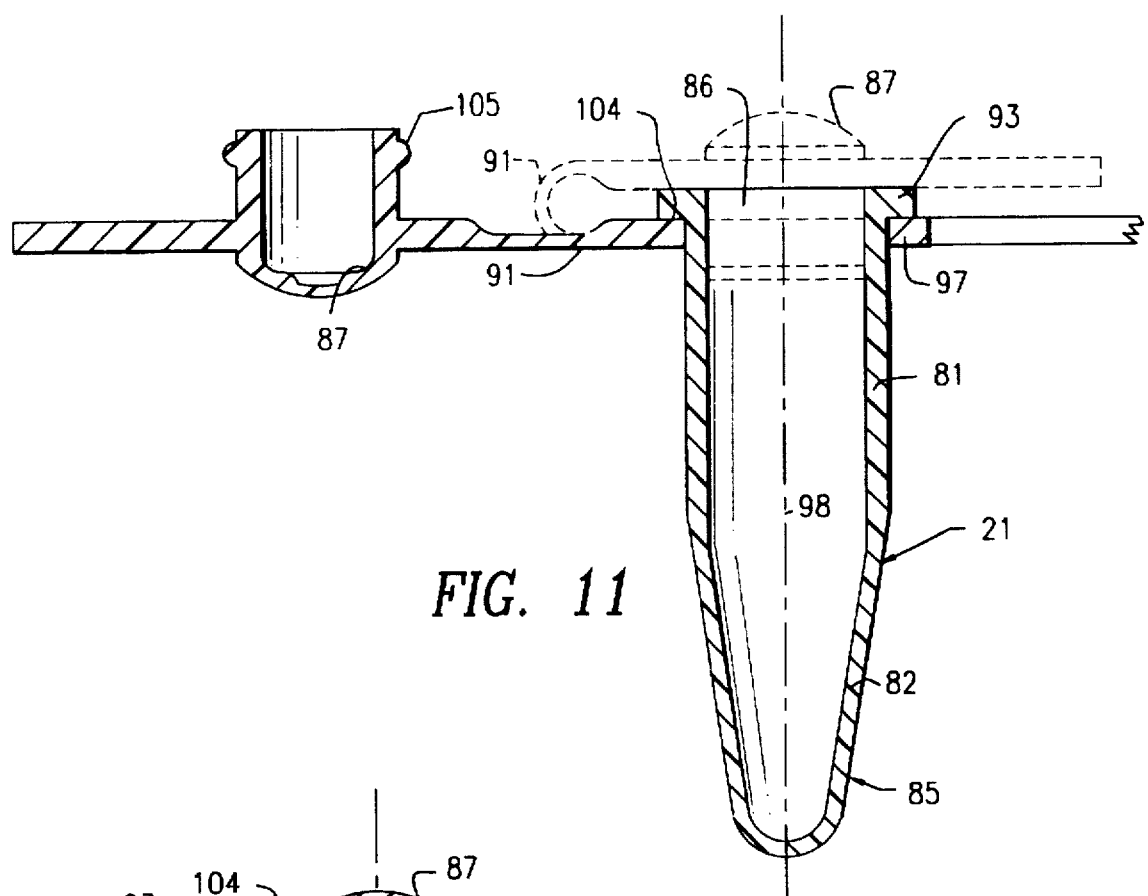
FIG. 11 is a section through a test tube 21 in FIG. 9 with open lid 87.
Figure 12:
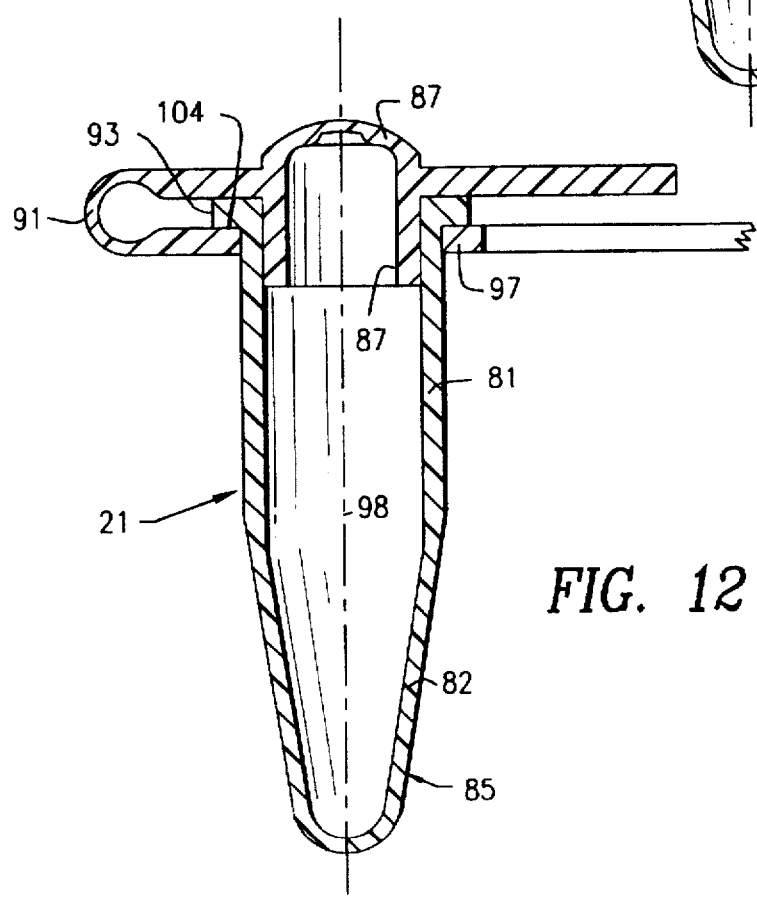
FIG. 12 is a section through a test tube 21 in FIG. 9 with closed lid 87.

When the two parts 92, 95 of the test tube arrangement 23 are brought together (FIG. 9), the flanges 93 on the test tubes 21 in one part 92 abut the top surfaces 104 of the rings 97 in the other part 95. As a result of the close fit between the cylindrical region 81 and the ring 97, the test tube arrangement 23 is relatively rigidly preassembled and can be filled with the appropriate samples. The lid 87 is then folded over and the cylindrical extension 105 thereof is held in sealing-tight manner in the openings 86 of the test tubes 21 (FIG. 10).

The webs 94, 96 provided in the aforementioned test-tube arrangement 23 give the arrangement sufficient flexibility for the test tubes 21 to be very easily inserted into the recesses 27 of the unit heater 33. If the arrangement 23 is rigid, such insertion can be difficult, even if there are only small deviations from the dimensions of the unit heater or of the test tube arrangement.

As a result of the two-part construction of the test tube arrangement 23, extreme economies of material can be made and, if advantageous, materials (typically plastics) having different properties can be used, to optimize results. This is important for throw away articles (the test tube arrangement is typically thrown away after use).

Analytical device with a thermal cycler

FIG. 13 shows an analytical device 1, designed for example, for performance of immunoassays.

In order to increase the volume of substances under analysis, present in the samples, to above the detection limit in the subsequent process of analysis, the analytical device incorporates a thermal cycler part 2 containing previously-described thermal cyclers 18 and 19 according to the invention, for working a DNA amplification process using the polymerase chain reaction.

In order to increase the productivity of the analytical device, that is, process a maximum number of samples per unit time, the number of prepared samples has to be adapted to the subsequent process times, to avoid any idle times. This is achieved for example, by two independently operating thermal cyclers 18 and 19, each capable of holding twelve reaction containers 21, and two standby stations 22, likewise each capable of holding twelve reaction containers 21 taken from one of the thermal cyclers 18, 19 at the end of the process therein.

The analytical device 1 may also contain all other equipment for the aforementioned immunoassays, for example, two racks 3, 4 holding reagents on a vibrating table 5, a rack 6 holding other reagents, three racks 7 containing throw away reaction containers 8, a temperature-controlled incubator 9 into which the reaction containers 8 are inserted, a washing device 11 and a photometer device 12 for determining the result of the test.

Test head of the analytical device

The samples, reagents, and reaction-holders are transferred by a head movable in an x-y coordinate system and containing a pipetting device 14 and a reaction container gripper 15, both movable in the z direction.

After DNA amplification in the reaction containers 21 in the thermal cyclers 18 and 19, the pipetting device 14 takes volumes of sample from the reaction containers 21 and delivers them to reaction containers 8 disposed in the racks 7. The volumes of samples delivered to the reaction containers 8 are investigated in immunoassays made by the analytical device.

Control unit of the analytical device

All required operations are controlled and coordinated by a central control unit (not shown) belonging to the analytical device. A control panel 16 or keyboard for inputting process parameters, and a display for displaying states of the process, are diagrammatically indicated. Data regarding the samples, recorded on the reaction containers for example, in a bar code, can be read into a store via a manually guided wand or scanner 17. Interfaces for a printer etc. (not shown) are provided.

The subject invention has been described in terms of its preferred embodiments. As such, one skilled in the art having read the present specification will become cognizant of numerous variations and alternative embodiments. For example, construction materials, computer controls, selection of thermally conductive materials, and configuration of the ring-like arrangement of chambers are readily variable. As a further example, the ring-like arrangement may be an oval, circle, semicircle or other arcuate configuration. These variants are to be considered within the scope and spirit of the invention, which is only to be limited by the claims that follow and their equivalents.

What is claimed is:

1. An automatic analytical device, which comprises:
    (a) a plurality of test tubes, each for containing a predetermined volume of a liquid reaction mixture, each of the plurality of test tubes being equipped with a pierceable closure;
    (b) a pipetting needle configured and dimensioned for piercing the pierceable closures and removing liquid reaction mixture from the test tubes;
    (c) means for moving the pipetting needle from a position outside of each test tube, through the piercable closure on the test tube, and into the test tube;
    (d) means for applying suction to the pipetting needle so as to enable the pipetting needle to withdraw liquid reaction mixture out of a given test tube when the pipetting needle is inside the given test tube and reaction mixture is present within the given test tube; and
    (e) a device for automatic performance of temperature cycles on the test tubes, which comprises:
        (1) a holder formed of a thermally conductive material and having an upper surface, a lower surface and a cylindrical outer wall, the holder having an array of chambers for holding the test tubes equipped with piercable closures, the chambers being disposed along an arc with each chamber having an opening located in the upper surface of the holder, each chamber being configured and dimensioned to receive one test tube equipped with a piercable closure, the holder being configured and dimensioned so that when test tubes having piercable closures are held in the array of chambers, the piercable closures of the test tubes can be accessed by a pipetting needle;
        (2) a computer-regulated automatic control system; and
        (3) means actuated by the automatic control system for cyclic alteration of the temperature of the holder.

2. The device according to claim 1, wherein the means for cyclic alteration of the temperature of the holder includes a cold- and heat-producing element in the form of at least one Peltier element which is in thermal contact with the bottom surface of the holder.

3. The device according to claim 1, wherein the means for cyclic alteration of the temperature of the holder includes at least one Peltier element which is configured and dimensioned to operate as a cold-producing element and which is in thermal contact with the bottom surface of the holder.

4. The device according to claim 2, wherein the at least one Peltier element has a central part and is pressed against the holder by spring-biased securing means positioned at the central part, which securing means comprises a spring pressed by a screw, the tension on the spring being adjustable by means of the screw.

5. The device according to claim 3, wherein the at least one Peltier element has a central part and is pressed against the holder by spring-biased securing means positioned at the central part, which securing means comprises a spring pressed by a screw, the tension on the spring being adjustable by means of the screw.

6. The device according to claim 1 further comprising a hinged lid having a heating element for heating the test tubes having piercable closures when such test tubes are held in the array of chambers, the lid having an opening for each chamber so that the pipetting needle can traverse each opening to access the pierceable closure of the test tube in the chamber.

7. The device of claim 6, wherein the hinged lid contains a closing and pressure means for securing the test tubes having piercable closures when such test tubes are held in the array of chambers.

8. The device according to claim 1 further comprising a heating element disposed around the holder along the periphery of the cylindrical outer wall of the holder.

9. The device according to claim 1 further comprising means for recognizing a marking on an arrangement of test tubes.

10. The device according to claim 6 further comprising a lifting-out device for facilitating removal of the test tubes from the chambers in the holder, the lifting-out device comprising an ejection lever having one end connected to the hinge of the lid and the other end free.

11. The device according to claim 10 further comprising an ejection disc which is secured to the lever and is concentric with the axis of symmetry of the holder, the disc having a peripheral arrangement of recesses for removing the test tubes from the chambers.

12. The device of claim 1, wherein the chambers are disposed along an arc that forms a complete circle.

13. The device of claim 1, wherein the chambers are disposed along an arc that forms a semi-circle.

* * * * *